United States Patent
Uhland et al.

(10) Patent No.: US 9,204,895 B2
(45) Date of Patent: Dec. 8, 2015

(54) MULTIPLE RESERVOIR DRUG DELIVERY DEVICE AND METHODS

(71) Applicant: PALO ALTO RESEARCH CENTER INCORPORATED, Palo Alto, CA (US)

(72) Inventors: Scott A. Uhland, San Jose, CA (US); Ramkumar Abhishek, Mountain View, CA (US); Eric Peeters, Mountain View, CA (US); Timothy J. Curley, San Carlos, CA (US); Felicia Linn, San Jose, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 0 days.

(21) Appl. No.: 14/577,252

(22) Filed: Dec. 19, 2014

(65) Prior Publication Data

US 2015/0105610 A1    Apr. 16, 2015

Related U.S. Application Data

(62) Division of application No. 13/629,159, filed on Sep. 27, 2012, now Pat. No. 9,005,108.

(51) Int. Cl.
*A61B 17/43*  (2006.01)
*A61M 5/145*  (2006.01)
(Continued)

(52) U.S. Cl.
CPC . *A61B 17/43* (2013.01); *A61D 7/00* (2013.01); *A61K 9/0004* (2013.01);
(Continued)

(58) Field of Classification Search
CPC ..... A61K 9/0004; A61K 9/0034; A61K 9/20; A61K 9/50; A61M 31/002; A61B 17/425; A61B 17/43; A61D 19/00; A61D 19/02
See application file for complete search history.

(56) References Cited

U.S. PATENT DOCUMENTS 4,304,232 A   12/1981  Michaels
4,308,867 A   1/1982   Roseman et al.
(Continued)

FOREIGN PATENT DOCUMENTS

DE    4130843 A1    3/1993
WO    94/01165 A1   1/1994
(Continued)

OTHER PUBLICATIONS

Bridges, et al., "Timed-Artificial Insemination in Beef Cows: What are the Options?," Purdue University Cooperative Extension Service, West Lafayette, IN (REV Mar. 2008).
(Continued)

*Primary Examiner* — Christine H Matthews
*Assistant Examiner* — Joshua D Lannu
(74) *Attorney, Agent, or Firm* — Sutherland Asbill & Brennan LLP

(57) ABSTRACT

Devices and methods are provided for drug delivery. The device may include a housing configured for intraluminal deployment into a human or animal subject and first and second reservoirs within the housing, each reservoir having an actuation end, an opposed release end, and a plug moveable from the actuation end toward the release end. First and second drug formulations may be contained in the first and second reservoirs, respectively. The device may also include one or more actuation systems configured to drive the first and second plugs so as to drive the first and second drug formulations from the first and second reservoirs. The housing may include a porous membrane sidewall in fluid communication with the release ends of the first and second reservoirs, the porous membrane sidewall being configured to distribute the first and second drug formulations driven from the first and second reservoirs.

10 Claims, 10 Drawing Sheets

(51) Int. Cl.
  *A61M 5/168* (2006.01)
  *A61M 31/00* (2006.01)
  *A61K 9/00* (2006.01)
  *A61D 7/00* (2006.01)
  *A61M 5/14* (2006.01)
  *A61M 5/155* (2006.01)
  *A61M 5/142* (2006.01)

(52) U.S. Cl.
  CPC ............. *A61K 9/0034* (2013.01); *A61M 5/145* (2013.01); *A61M 5/1408* (2013.01); *A61M 5/155* (2013.01); *A61M 5/16827* (2013.01); *A61M 31/00* (2013.01); *A61M 2005/14204* (2013.01); *A61M 2210/1042* (2013.01); *A61M 2210/1085* (2013.01); *A61M 2210/1433* (2013.01); *A61M 2210/1475* (2013.01)

(56) References Cited

U.S. PATENT DOCUMENTS

| | | |
|---|---|---|
| 4,402,695 A | 9/1983 | Wong |
| 4,687,423 A | 8/1987 | Maget et al. |
| 4,886,514 A | 12/1989 | Maget |
| 4,902,278 A | 2/1990 | Maget et al. |
| 5,002,540 A | 3/1991 | Brodman et al. |
| 5,062,834 A | 11/1991 | Gross et al. |
| 5,090,963 A | 2/1992 | Gross et al. |
| 5,112,614 A | 5/1992 | Magruder et al. |
| 5,135,499 A | 8/1992 | Tafani et al. |
| 5,318,557 A | 6/1994 | Gross |
| 5,354,264 A | 10/1994 | Bae et al. |
| 5,415,629 A | 5/1995 | Henley |
| 5,522,804 A | 6/1996 | Lynn |
| 5,589,457 A * | 12/1996 | Wiltbank et al. ............ 514/10.1 |
| 5,593,552 A | 1/1997 | Joshi et al. |
| 5,780,058 A | 7/1998 | Wong et al. |
| 5,816,248 A | 10/1998 | Anderson et al. |
| 5,928,195 A | 7/1999 | Malamud et al. |
| 5,951,538 A | 9/1999 | Joshi |
| 6,030,375 A | 2/2000 | Anderson et al. |
| 6,086,909 A | 7/2000 | Harrison et al. |
| 6,139,538 A | 10/2000 | Houghton et al. |
| 6,183,434 B1 | 2/2001 | Eppstein |
| 6,322,532 B1 | 11/2001 | D'Sa et al. |
| 6,352,524 B1 | 3/2002 | Bunt et al. |
| 6,423,039 B1 | 7/2002 | Rathbone et al. |
| 6,444,224 B1 | 9/2002 | Rathbone et al. |
| 6,450,991 B1 * | 9/2002 | Bunt et al. .................... 604/143 |
| 6,532,386 B2 | 3/2003 | Sun et al. |
| 6,591,133 B1 | 7/2003 | Joshi |
| 6,638,246 B1 | 10/2003 | Naimark et al. |
| 6,756,053 B2 | 6/2004 | Zhang et al. |
| 6,776,164 B2 | 8/2004 | Bunt et al. |
| 6,805,877 B2 | 10/2004 | Massara et al. |
| 6,835,392 B2 | 12/2004 | Hsu et al. |
| 6,962,579 B2 | 11/2005 | Jellie |
| 6,978,172 B2 | 12/2005 | Mori et al. |
| 7,004,171 B2 | 2/2006 | Benita et al. |
| 7,083,590 B1 * | 8/2006 | Bunt et al. ...................... 604/30 |
| 7,486,989 B2 | 2/2009 | Sun et al. |
| 7,497,855 B2 | 3/2009 | Ausiello et al. |
| 7,732,408 B2 * | 6/2010 | Josephson et al. ............ 514/10.3 |
| 2002/0010414 A1 | 1/2002 | Coston et al. |
| 2002/0045883 A1 | 4/2002 | Jellie |
| 2003/0018295 A1 | 1/2003 | Henley et al. |
| 2003/0130558 A1 | 7/2003 | Massara et al. |
| 2003/0219472 A1 | 11/2003 | Pauletti et al. |
| 2004/0059388 A1 | 3/2004 | Herbst et al. |
| 2004/0082937 A1 | 4/2004 | Ausiello et al. |
| 2004/0087893 A1 | 5/2004 | Kwon |
| 2004/0219192 A1 | 11/2004 | Horstmann et al. |
| 2005/0054969 A1 | 3/2005 | Hoff et al. |
| 2005/0124875 A1 | 6/2005 | Kawano et al. |
| 2005/0244502 A1 | 11/2005 | Mathias et al. |
| 2005/0267440 A1 | 12/2005 | Herman et al. |
| 2006/0024358 A1 | 2/2006 | Santini et al. |
| 2006/0184092 A1 | 8/2006 | Atanasoska et al. |
| 2007/0038181 A1 | 2/2007 | Melamud et al. |
| 2007/0225634 A1 | 9/2007 | Ferren et al. |
| 2007/0269385 A1 | 11/2007 | Yun et al. |
| 2008/0004564 A1 | 1/2008 | Smith |
| 2008/0004596 A1 | 1/2008 | Yun et al. |
| 2008/0262412 A1 | 10/2008 | Atanasoska et al. |
| 2008/0269666 A1 | 10/2008 | Wang et al. |
| 2009/0131737 A1 | 5/2009 | Ferren et al. |
| 2009/0171315 A1 | 7/2009 | Versi |
| 2009/0306633 A1 | 12/2009 | Trovato et al. |
| 2011/0087155 A1 | 4/2011 | Uhland et al. |
| 2011/0087192 A1 | 4/2011 | Uhland et al. |
| 2011/0087195 A1 | 4/2011 | Uhland et al. |
| 2012/0046518 A1 * | 2/2012 | Yoakum et al. ................ 600/35 |
| 2013/0211272 A1 | 8/2013 | Rosenshein |
| 2014/0088345 A1 | 3/2014 | Uhland et al. |
| 2014/0088486 A1 | 3/2014 | Uhland et al. |

FOREIGN PATENT DOCUMENTS

| | | |
|---|---|---|
| WO | 94/18952 A1 | 9/1994 |
| WO | 97/41831 A1 | 11/1997 |
| WO | 01/12101 A1 | 2/2001 |
| WO | 2005/056708 A2 | 6/2005 |
| WO | 2005/089728 A2 | 9/2005 |
| WO | 2007/041119 A1 | 4/2007 |
| WO | 2007/047811 A2 | 4/2007 |
| WO | 2007/140416 A2 | 12/2007 |
| WO | 2009/081411 A2 | 7/2009 |
| WO | 2010/048478 A2 | 4/2010 |

OTHER PUBLICATIONS

Hashimoto, et al., "Oxidative stress induces gastric epithelial permeability through claudin-3." Biochemical and Biophysical Research Communications (2008), vol. 376, pp. 154-157.

Seth, et al., "Probiotics ameliorate the hydrogen peroxide-induced epithelial barrier disruption by a PKC-and MAP kinase-dependent mechanism," Am J Physiol Gastrontest Liver Physiol (2008), vol. 294, pp. G1060-G1069. Retrieved from http://www.ajpgi.org on Jul. 28, 2009.

Kadajji, et al., "Water Soluble Polymers for Pharmaceutical Applications." Polymers (2011), vol. 3, pp. 1972-2009.

Fatakdawala, Hussain et al., "Hydrogen peroxide mediated transvaginal drug delivery," International Journal of Pharmaceutics 409 (2011) 121-127.

International Search Report and Written Opinion for PCT/US2013/051517 mailed Oct. 16, 2013.

SáaFilho, O. G. et al., "Fixed-time artificial insemination with estradiol and progesterone for Bos indicus cows II: Strategies and factors affecting fertility," Science Direct, Theriogenology 72 (2009) 210-218.

* cited by examiner

MULTIPLE RESERVOIR DRUG DELIVERY DEVICE AND METHODS

CROSS-REFERENCE TO RELATED APPLICATIONS

This application is a divisional of U.S. application Ser. No. 13/629,159, filed Sep. 27, 2012, which is incorporated herein by reference in its entirety.

FIELD

The present disclosure is generally in the field of drug delivery devices and methods, and more particularly to devices and methods for the transmucosal delivery of multiple drugs to human or animal subjects.

BACKGROUND

Controlled delivery of multiple drugs from a single device is an area of interest because of the potential of delivering a series of drugs in a treatment regimen in a specific release profile. For example, current fixed time artificial insemination (FTAI) treatments for cattle require the administration of multiple drugs at specific times. These treatments result in significant time spent driving, herding, and chuting the cattle, cause stress and increased cortisol levels in the subjects, and require multiple drug delivery devices and precise drug administration timing.

Transmucosal drug delivery is an area of interest because of the potential of delivering systemically-acting drugs with a high relative bioavailability by avoiding first-pass metabolism effects, the potential of locally delivering therapeutic agents to a site of interest, and the convenience of application routes. Some of the possible sites for transmucosal drug delivery include the buccal, nasal, vaginal, and rectal administration routes.

Accordingly, it would be desirable to provide improved devices and methods to transmucosally administer multiple drug formulations from a single device to human patients or animal subjects.

SUMMARY

In one aspect, a device for drug delivery is provided, which includes a housing configured for intraluminal deployment into a human or animal subject. A first reservoir having an actuation end and an opposed release end is located within the housing and includes a first drug formulation. A second reservoir having an actuation end and an opposed release end is located within the housing and includes a second drug formulation. A first plug is provided within the first reservoir and is moveable from the actuation end toward the release end, and a second plug is provided within the second reservoir and is moveable from the actuation end toward the release end. The device includes one or more actuation systems configured to drive the first and second plugs so as to drive the first and second drug formulations from the first and second reservoirs. The housing includes a porous membrane sidewall in fluid communication with the release ends of the first and second reservoirs, and the porous membrane sidewall is configured to distribute the first and second drug formulations driven from the first and second reservoirs, respectively, to a tissue area adjacent the porous membrane sidewall when the device is deployed intraluminally in the human or animal subject.

In another aspect, a method of drug delivery is provided, which includes deploying a drug delivery device into a mucosal lumen of a human or animal subject, actuating one or more actuation systems to drive first and second drug formulations out of first and second reservoirs and into a porous membrane sidewall, and releasing the first and second drug formulations from the porous membrane sidewall to the mucosal lumen, wherein the drug delivery device includes a first reservoir containing a first drug formulation, a second reservoir containing a second drug formulation, and a porous membrane sidewall adjacent the mucosal lumen.

In yet another aspect, a method is provided for fixed time artificial insemination, which includes deploying a drug delivery device into a vaginal lumen of an animal subject; driving a first drug formulation out of a first reservoir at a first time; driving a second drug formulation out of a second reservoir at a second time, which is after the first time; driving a third drug formulation out of a third reservoir at a third time, which is after the second time; and artificially inseminating the animal subject at a fourth time, which is after the third time. In an embodiment, the drug delivery device includes a housing containing (i) a first reservoir containing a first drug formulation comprising a gonadotropin-releasing hormone, (ii) a second reservoir containing a second drug formulation comprising a prostaglandin, (iii) a third reservoir containing a third drug formulation comprising a gonadotropin-releasing hormone, (iv) a porous membrane sidewall adjacent the vaginal lumen, and (v) one or more actuation systems configured to drive the first, second, and third drug formulations from the first, second, and third reservoirs.

DETAILED DESCRIPTION

The implantable devices and methods of drug administration described herein provide for the storage and controlled delivery of multiple drug formulations. The devices are advantageously configured to separately store multiple drug formulations, thereby minimizing the risk of contamination, and to precisely dispense the drug formulations according to a specific release timing profile. These devices and methods desirably provides for a single, multi-reservoir device to deliver a series of drug doses to a patient or animal at prescribed times. The devices and methods can significantly increase the accuracy and efficiency of delivering multiple agents to subjects, which can be particularly advantageous, for example, in large scale animal husbandry operations, such as fixed time artificial insemination using common estrous synchronization protocols.

Figure 1:
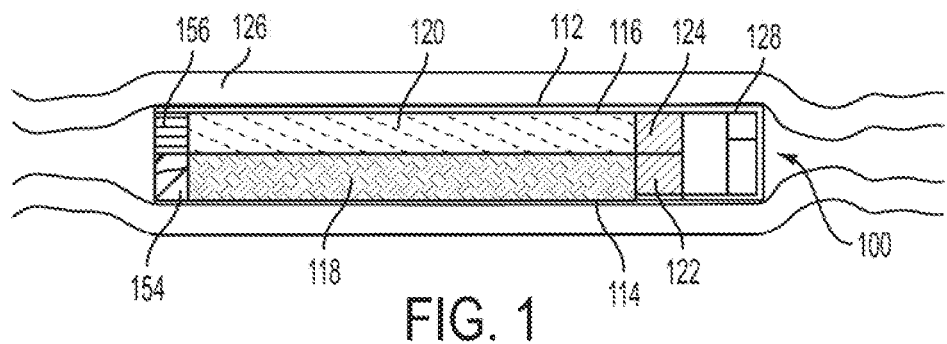
FIG. 1 is a cross-sectional view, illustrating one embodiment of a drug delivery device having two reservoirs, each reservoir containing a drug formulation and having a static threshold barrier, in a tissue lumen.

In one aspect, a device for drug delivery is provided. As shown in FIG. 1, the device 100 includes a housing 112 configured for intraluminal deployment into a human or animal subject. The term "intraluminal," as used herein, refers to placement within a body cavity, channel, tube, or the like, having a mucosal wall. The term includes, but is not limited to, sites in the reproductive tract, such as intravaginal, cervical, or intrauterine, and the gastrointestinal tract, such as intrarectal.

Figure 9:
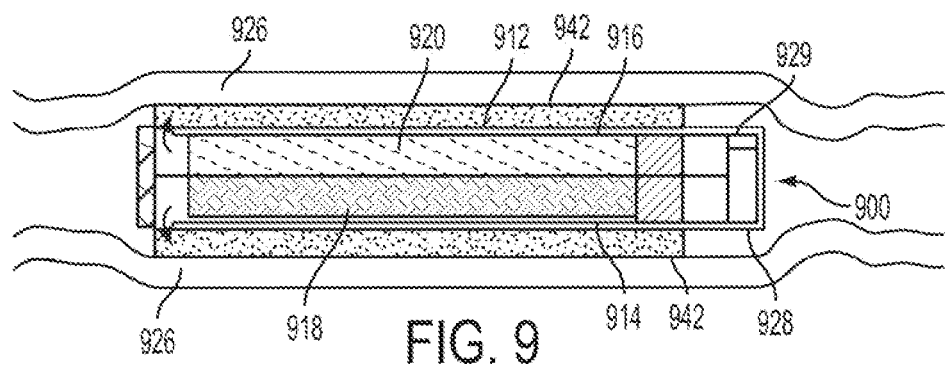
FIG. 9 is a cross-sectional view, illustrating one embodiment of a drug delivery device having a porous membrane sidewall.

The device 100 includes a first reservoir 114 and a second reservoir 116 located within the housing 112. The first and second reservoirs 114, 116 each have an actuation end portion and an opposed release end portion. A first drug formulation 118 is disposed within first reservoir 114 and a second drug formulation 120 is disposed within the second reservoir 116. The device 100 also includes a first plug 122 within the first reservoir 114 and a second plug 124 within the second reservoir 116. The first and second plugs 122, 124 are movable from the actuation end toward the release end of the first and second reservoirs 114, 116 to drive the first and second drug formulations 118, 120 out of the first and second reservoirs 114, 116. One or more actuation systems 128 are configured to drive the first and second plugs 122, 124 so as to drive the first drug formulation 118 from the first reservoir 114 and drive the second drug formulation 120 from the second reservoir 116. As shown in FIG. 9, the device 900 may include a porous membrane sidewall 942 in fluid communication with the release ends of the first and second reservoirs 914, 916, the porous membrane sidewall 942 being configured to distribute the first and second drug formulations 918, 920 driven from the first and second reservoirs 914, 916, respectively, to a tissue area 926 adjacent the porous membrane sidewall 942 when the device 900 is deployed intraluminally in the human or animal subject.

In another aspect, a method of drug delivery is provided. The method may include (i) deploying a drug delivery device having a porous membrane sidewall and first and second reservoirs containing first and second drug formulations, respectively, into a mucosal lumen of a human or animal subject, (ii) actuating one or more actuation systems to drive the first and second drug formulations out of the first and second reservoirs; and (iii) releasing the first and second drug formulations from the porous membrane sidewall to the mucosal lumen adjacent thereto.

Various embodiments and features of the drug delivery devices and methods are described in greater detail hereinafter.

Housing

Figure 7A:
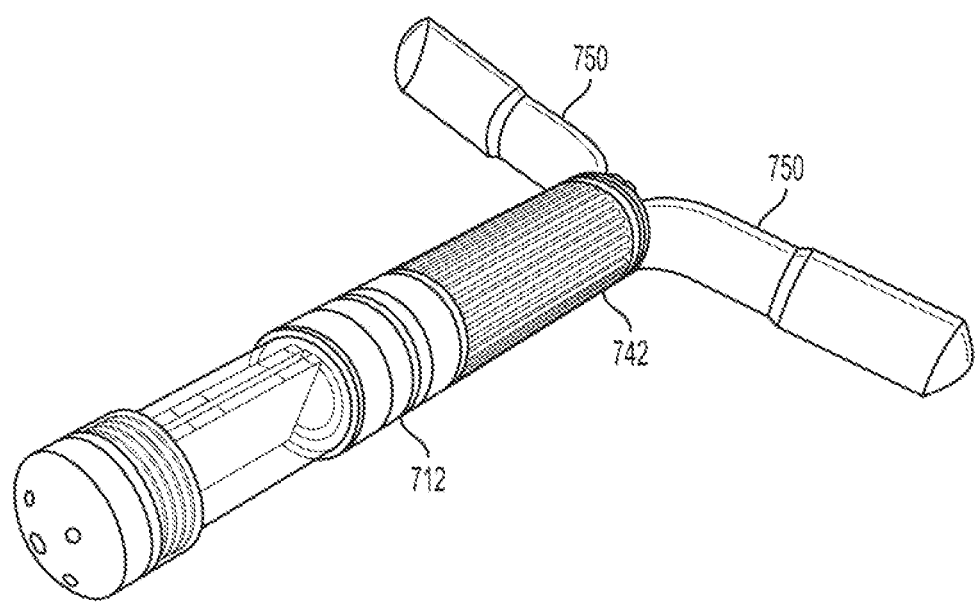
FIG. 7A is a perspective view, illustrating one embodiment of a drug delivery device.
Figure 7B:
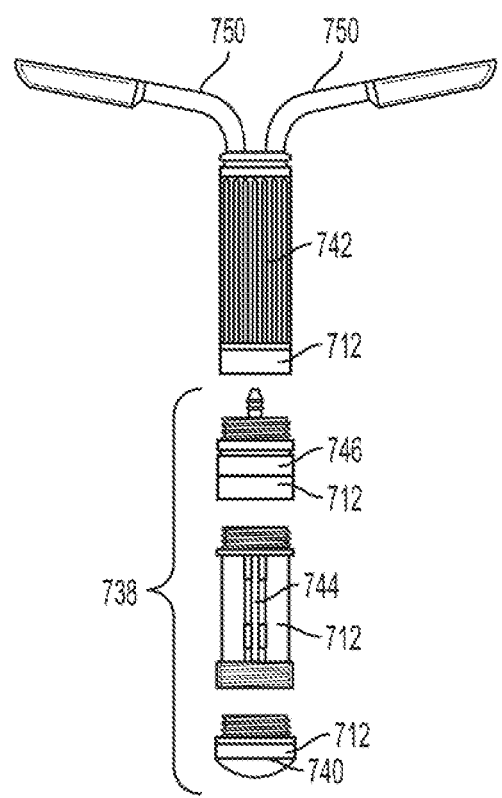
FIG. 7B is a partially exploded plan view, illustrating the drug delivery device of FIG. 7A.
Figure 7C:
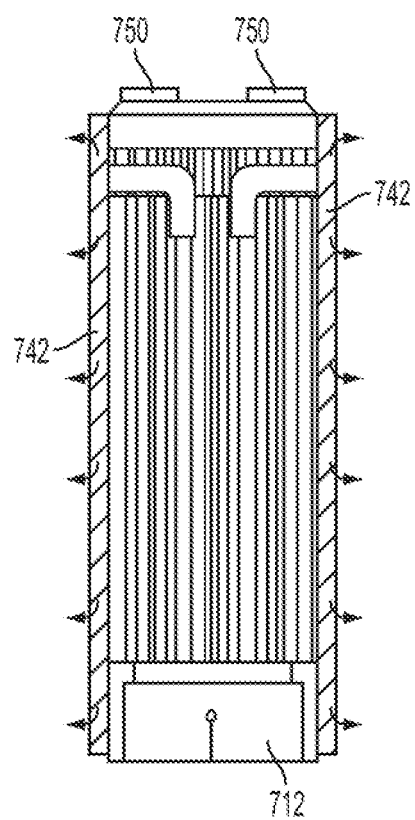
FIG. 7C is a cross-sectional view, illustrating the porous membrane sidewall of the drug delivery device of FIGS. 7A and 7B.

The device includes a housing generally configured to facilitate deployment of the drug delivery device within a lumen of a human or animal subject. The housing configuration is based upon the particular luminal site and human or animal anatomical considerations, for deployment with minimal discomfort to the patient. In certain embodiments, the device may be placed within the lumen by insertion into the lumen via an exterior body orifice. Accordingly, in certain embodiments, the housing is shaped and dimensioned to allow insertion and placement, i.e., deployment, of the device within the intended lumen via the exterior body orifice. For example, the housing may be shaped and dimensioned for vaginal, cervical, uterine, or rectal insertion and placement. As shown in FIGS. 7A-7C, the housing 712 may include an elongated, substantially cylindrical portion having wing-like portions, or arms, 750 extending therefrom. For example, this configuration may be appropriate for vaginal device deployment in livestock, such as cattle, sheep, etc.

The materials of construction, size, shape, surface features, and other characteristics of the housing are configured such that the device can be deployed into the lumen, retained securely in the lumen during operation of the device, and retrieved from the lumen following operation of the device or when otherwise desired to be removed. For example, the device may be removed between the delivery of individual drug formulations, following the delivery of several drug formulations, or following the completion of a course of treatment of multiple drug formulations. The device may be deployed until the drug formulation payload is depleted.

The housing may be formed of any biocompatible material. Moreover, the housing material may be resistant to degradation in the mucosal environment of the lumen. Examples of suitable housing materials include stainless steel, titanium, and biocompatible polymers, such as polypropylene, polyethylene, or other common polymers, such as nylon having a biocompatible outer layer, e.g., silicone. The housing material may include a coating to enhance biocompatibility and/or operation of the device.

Reservoirs and Contents

At least two reservoirs are located within the housing. The reservoirs each have an actuation end and an opposed release end. The actuation ends may be operably connected to the actuation system. The release ends may include structures, such as one-way flow valves, for controlling the release of the drug formulations to the luminal tissue adjacent the release ends.

The reservoirs may be disposed within the housing such that they are parallel to each other. The reservoirs may each be defined by an inner surface of an elongated annular tube. The reservoirs may also have a combined shape similar to that of the housing and be configured such that the reservoirs occupy a majority of the volume of the housing. In certain embodiments, the reservoirs are elongated and have a circular cross-sectional shape. Other cross-sectional shapes are also envisioned.

Figure 6:
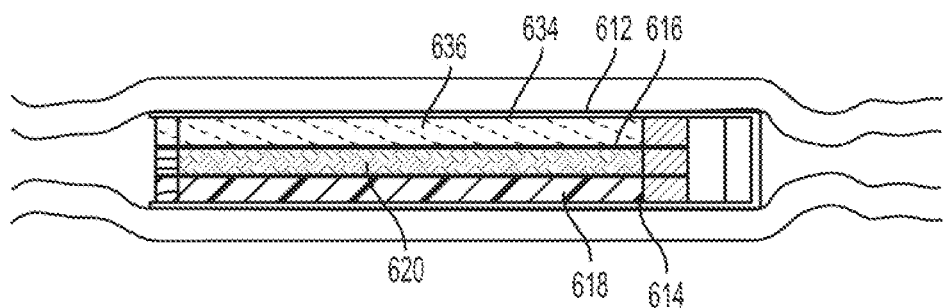
FIG. 6 is a cross-sectional view, illustrating one embodiment of a drug delivery device having three reservoirs, each reservoir containing a drug formulation and having a static threshold barrier, in a tissue lumen.

In one embodiment, the first and second reservoirs contain first and second drug formulations, respectively. The device may include more than two reservoirs located within the housing. For example, as shown in FIG. 6, the device may include a third reservoir 634 located within the housing 612 and containing a third drug formulation 636. Each reservoir may also contain multiple drug formulations. In particular embodiments, the multiple drug formulations are ones selected to work in concert, but beneficially are administered in series, for example in a separated or overlapping schedule.

Figure 3:
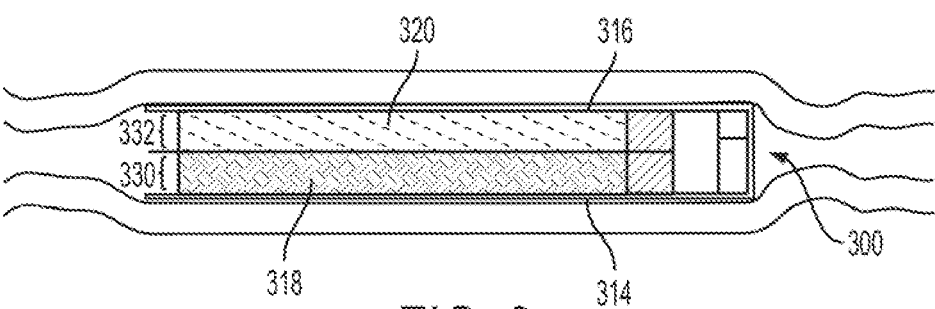
FIG. 3 is a cross-sectional view, illustrating one embodiment of a drug delivery device having two reservoirs, each reservoir containing a drug formulation, in a tissue lumen.

In certain embodiments, as shown in FIG. 3, the first reservoir 314 contains first drug formulation 318 while the second reservoir 316 contains second drug formulation 320.

The reservoirs also each include a plug which is movable from the actuation end of the reservoir toward the release end of the reservoir. The plugs are configured to drive the drug formulations out of the reservoirs. The plugs generally are positioned between the actuation system and the drug formulations within each reservoir. The plugs may include a fluid layer or a solid barrier. For example, the first and second plugs may include an inert gel. Inert gels may include polyvinyl alcohol (PVA), poly(ethylene glycol) (PEG), hyaluronic acid (HA), cellulose, polyvinyl pyrrolidone (PVP), polyacrylic acid (PAA), polyethylene oxide (PEO), polyp-phenylene oxide) (PPO), polyacrylamides, N-(2-hydroxypropyl) methacrylamide (HPMA), divinyl ether-maleic anhydride (DIVEMA), poly(2-alkyl-2-oxazolines), polyphosphates, polyphosphazenes, xanthan gum, polysaccharides, chitosan derivatives, carrageenan, cellulose ethers, starches, formulations of silicone elastomers such as polydimethylsiloxane (PDMS), or combinations thereof.

Alternatively, the plugs may include a biocompatible plunger. Plungers may include higher molecular weight polyvinyl alcohol (PVA), poly(ethylene glycol) (PEG), hyaluronic acid (HA), cellulose, polyvinyl pyrrolidone (PVP), polyacrylic acid (PAA), polyethylene oxide (PEO), poly(p-phenylene oxide) (PPO), polyacrylamides, N-(2-hydroxypropyl) methacrylamide (HPMA), divinyl ether-maleic anhydride (DIVEMA), poly(2-alkyl-2-oxazolines), polyphosphates, polyphosphazenes, xanthan gum, polysaccharides, chitosan derivatives, carrageenan, cellulose ethers, starches, formulations of silicone elastomers such as polydimethylsiloxane (PDMS), or combinations thereof.

In one embodiment, the first and second plugs each include an expandable membrane. For example, the expandable membrane may include a balloon-like structure that expands or inflates to drive the drug formulations out of the reservoirs. The balloon like structure may be an elastomer, such as latex, nitrile or urethane based, or it may be a collapsed balloon, such as a thin metallized polymer sheet, e.g., polyester or polyethylene. Alternatively, the drug formulation may be contained within the balloon-like structure such that upon actuation, the actuation pressure collapses the balloon-like structure and the drug formulation is forced out of the reservoir. For example, the actuation may roll up, compress, or otherwise collapse the flexible reservoir (e.g., balloon) on itself to forcibly displace the contents from the reservoir.

In a particular embodiment, the plugs also sealingly engage with, and slide with respect to, the inner walls of the reservoirs. The plugs may function as pistons.

Release Structure

In embodiments, the device is configured to deliver the drug formulations to the mucosal tissue of the lumen in which the device is deployed. The drug formulations are released from the release end portions of the reservoir, toward which the plug drives the drug formulations. The release end portions of the reservoirs may be configured, e.g., may include further fluid passageway/directing structures, such as channels, to release the drug formulations from the device axially, radially, or a combination thereof. The release end of the reservoirs may also include one-way fluidic structures, such as umbrella valves, duck bill valves and crack valves, to control the direction of flow (toward tissue) within the device and resist reverse flow. Such valves may be constructed of silicone or other materials.

Figure 4A:
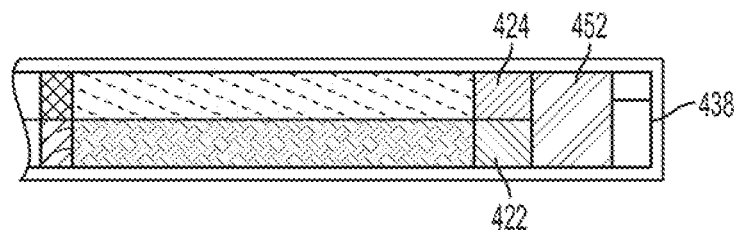
FIG. 4A is a cross-sectional view, illustrating one embodiment of a drug delivery device prior to actuation.
Figure 4B:
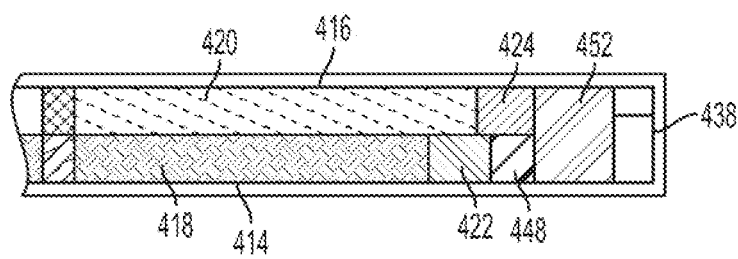
FIG. 4B is a cross-sectional view, illustrating the drug delivery device of FIG. 4A upon actuation.
Figure 4C:
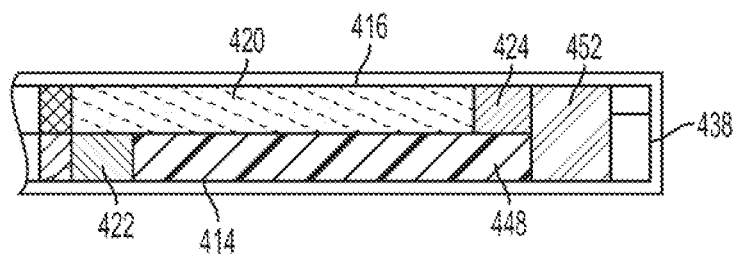
FIG. 4C is a cross-sectional view, illustrating the drug delivery device of FIG. 4A at a first later time following actuation.
Figure 4D:
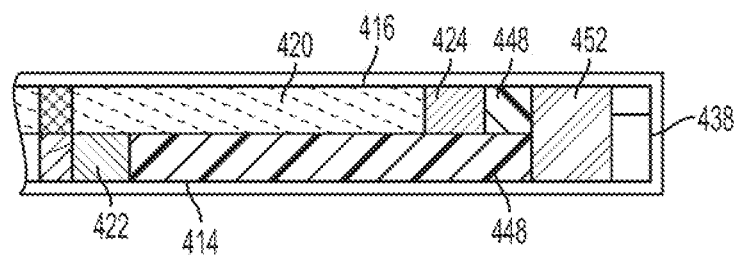
FIG. 4D is a cross-sectional view, illustrating the drug delivery device of FIG. 4A at a second later time following actuation.
Figure 4E:
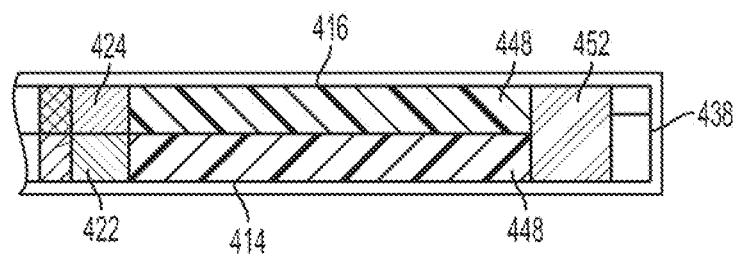
FIG. 4E is a cross-sectional view, illustrating the drug delivery device of FIG. 4A at a third later time following actuation.
Figure 5:
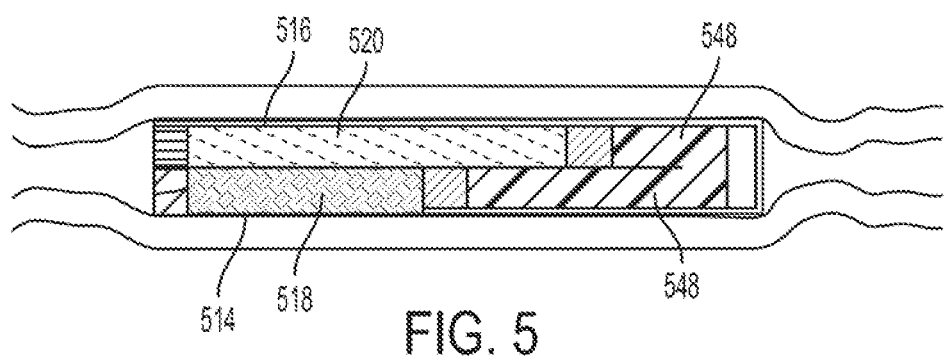
FIG. 5 is a cross-sectional view, illustrating one embodiment of a drug delivery device having two reservoirs, each reservoir containing a drug formulation and having a static threshold barrier, in a tissue lumen.

In certain embodiments, each reservoir includes a structure at the release end for controlling the release kinetics of the drug formulations. The configuration and characteristics of the structure at the release end of the each reservoir may be determined based on the temporal drug release profile desired. For example, as shown in FIG. 4B-4C, the release end structure may be configured such that upon actuation, release of the first drug formulation 418 from the first reservoir 414 is completed before any of the second drug formulation 420 is released from the second reservoir 416. Alternatively, as shown in FIG. 5, the release end structure may be configured such that upon actuation, release of the first drug formulation 518 from the first reservoir 514 overlaps with release of the second drug formulation 520 from the second reservoir 516.

Such structures may also function to redirect or spread the drug formulation across a greater area of the tissue lumen. For example, the device may include a porous membrane sidewall configured to diffuse and distribute the drug formulations released from the reservoirs to the luminal tissue. For example, the porous membrane sidewall may include a polycarbonate, polypropylene, PFTE, or polyethylene membrane, or any combination of laminates thereof.

FIG. 1 shows a configuration of a drug delivery device 100 in which the first reservoir 114 includes a first static threshold barrier 154 at the release end and the second reservoir 116 includes a second static threshold barrier 156 at the release end. For example, the first threshold barrier may include a first porous material while the second static threshold barrier includes a second porous material. In certain embodiments, the first porous material has a lower porosity than the second porous material such that the first drug formulation may be driven from the first reservoir before the second drug formulation is driven from the second reservoir. For example, the first porous material may have a porosity that is at least about 50% lower than the porosity of the second porous material. This may be achieved by controlling (i) the pore size, for example, from about 0.2 microns to about 200 microns, (ii) the pore volume fraction, for example from about 30% to about 70%, or (iii) a combination of (i) and (ii).

Figure 2:
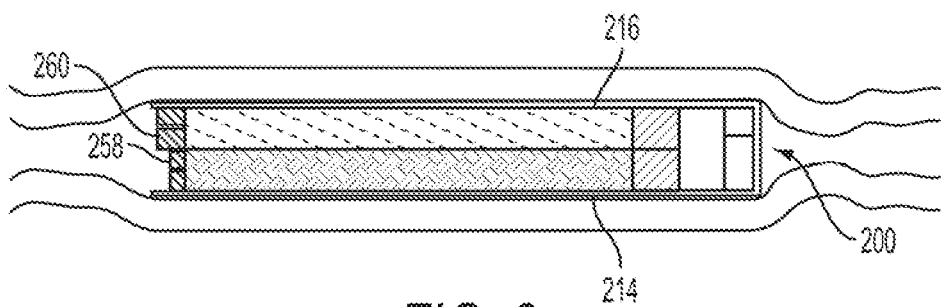
FIG. 2 is a cross-sectional view, illustrating one embodiment of a drug delivery device having two reservoirs, each reservoir containing a drug formulation and having an end cap, in a tissue lumen.

FIG. 2 shows a configuration of a drug delivery device 200 in which the first reservoir 214 includes a first end cap 258 at the release end and the second reservoir 216 includes a second end cap 260 at the release end. The first end cap may have a first aperture therein and the second end cap may have a second aperture therein. In certain embodiments, the length of the second aperture through the second end cap is at least 100% greater than the length of the first aperture through the first end cap. For example, suitable aperture lengths may be from about 10 μm to about 2 cm. For example, the apertures may be sized such that the first drug formulation may be driven from the first reservoir before the second drug formulation is driven from the second reservoir. For example, resistance to flow will increase with decreasing channel and increasing length according to Darcy's Law $$Q = \frac{-kA}{\mu} \frac{(P_b - P_a)}{L}$$

where Q represents volumetric flow rate, k represents the permeability constant (geometry dependent), A represents cross sectional area, L represents length, μ represents viscosity, and $P_b$–$P_a$ represents the driving pressure. Thus, decreasing A, increasing L, and increasing μ may decrease flow within a reservoir. Furthermore, by providing variable permeability constants, for example by removing a barrier such as by melting, or providing a one-way valve that deforms at a critical pressure, A and k may be increased such that flow is increased.

FIG. 3 shows a configuration of a drug delivery device 300 in which the first and second reservoirs 314, 316 include first and second outlets 330, 332 at the release ends of the reservoirs. In one embodiment, a ring of outlets is provided at the release end of the reservoir. For example, a ring of outlets may be radially positioned at the release end portions of the reservoirs. In certain embodiments, the first drug formulation is a fluid having a first viscosity and the second drug formulation is a fluid having a second viscosity. For example, the second viscosity may be more than 50% greater than the first viscosity such that the first drug formulation may be driven from the first reservoir before the second drug formulation is driven from the second reservoir. For example, suitable viscosities of the fluid drug formulations may be from about 0.1 cps to about 10 cps. In certain embodiments, as shown in FIG. 9, the housing 912 includes a porous membrane sidewall 942 in fluid communication with the release ends of the first and second reservoirs 914, 916. The porous membrane sidewall may be configured to distribute the drug formulations driven from the reservoirs to a tissue area adjacent the porous membrane sidewall when the device is deployed intraluminally in a human or animal subject. For example, the porous membrane sidewall 942 may be configured to distribute the first and second drug formulations 918, 920 driven from the first and second reservoirs 914, 916 to a tissue area 926. The arrows show how the drug formulations flow out of the reservoirs through radial outlets and into the porous membrane sidewall.

The devices shown in FIGS. 1-6 could further include radial outlets and/or a porous membrane sidewall (not shown) as described herein, for example as shown in FIG. 9.

The porous membrane sidewall may maximize the area of tissue which is exposed to the drug formulation by diffusing the drug formulation and distributing it across a large porous area on the outer housing of the device. The surface area of the porous membrane sidewall, and therefore the tissue surface to be treated, may be adjusted depending upon the targeted species and drug formulation to be delivered. In one embodiment, the surface area of the porous membrane sidewall ranges from 5% to 75% of the available mucosal tissue area. The porous membrane sidewall may also provide a reproducible wettable surface condition that reduces variability in the dosed tissue and variability in the delivered drug formulation doses. Such features may be beneficial over conventional technologies having individual ports for each drug to be dispensed. Such conventional devices may suffer from random delivery patterns and a lack of control over drug and tissue exposure, resulting in highly variable dosing.

In one embodiment, the porous membrane sidewall operates as a fluidic valve. For example, the porous membrane sidewall may have a pore structure and chemistry such that a positive pressure is required to initiate flow of the drug solution through the porous membrane sidewall. This thresholding pressure may be tuned by controlling the average pore size of the membrane's pore structure, as well as the contact angle of the drug solution on the surface of the membrane material. For example, the porous membrane sidewall may be a fluidic valve configured such that a critical threshold pressure from about 0.1 psi to about 100 psi is required to distribute the first and second drug formulations to the tissue area.

The pore structure may be any microstructure representative of an open pore structure. This may be a single layer of pores that expend from one surface of the membrane through to the opposing surface of the membrane. Alternatively, the pore structure may be a randomly packed structure of interconnected pores or a highly ordered, closed packed pores structure. For example, the porous membrane sidewall may have an average pore size from about 0.2 μm to about 25 μm.

In certain embodiments, the porous membrane sidewall acts as an aseptic barrier. For example, the porous membrane sidewall may be configured to substantially prohibit infiltration into the device of bacteria having a size in excess of the effective average pore size of the porous membrane sidewall.

The membrane may also be constructed of two or more dissimilar materials serving different functions outlined above. For example, a PTFE and polyethylene laminate structure may be used to achieve effective drug solution spreading, antimicrobial delivery, and valving. Alternatively, a composite material may be constructed to achieve these desired functions for drug solutions having differing wetting characteristics. This may be achieved, for example, by using interwoven porous sheets constructed of a predetermined ratio of hydrophobic to hydrophilic materials.

In certain embodiments, upon generation of a positive pressure via the actuation mechanism, the drug formulations are driven from the reservoirs and through the porous membrane sidewall. Once the pressure is reduced, the wetting condition will become thermodynamically unfavorable and flow will stop.

In certain embodiments, the porous membrane sidewall provides a surface that is in primary contact with tissue and therefore is composed of biocompatible materials. For example, the porous membrane sidewall may include a polypropylene membrane. Other suitable porous membrane sidewall materials include, but are not limited to, polyethersulfone, polycarbonate, polyethylene terephthalate, polyvinylidene fluoride, mixed cellulose ester, nylon 6,6, polytetrafluoroethylene, and combinations thereof.

In certain embodiments, the porous membrane sidewall substantially surrounds housing about the first and second reservoirs. For example, the porous membrane sidewall may be cylindrical. In certain embodiments, the porous membrane sidewall includes a first portion adjacent the release ends of the reservoirs and a second portion adjacent the actuation ends of the reservoirs such that the drug formulations are distributed from both the first and second portions of the porous membrane sidewall.

Actuation System

The device includes one or more actuation systems which are configured to drive the plugs and in turn drive the drug formulations from the reservoirs. In one embodiment, only one of the one or more actuation systems may be configured to drive the first and second plugs so as to drive the first drug formulation from the first reservoir and subsequently drive the second drug formulation from the second reservoir. In another embodiment, multiple actuation systems may be configured to drive multiple plugs so as to drive multiple drug formulations from multiple reservoirs.

The one or more actuation systems may be operably connected to the actuation ends of each of the reservoirs. Generally, each actuation system is configured to drive the plugs via a positive displacement process. The term "positive displacement," as used herein, refers to any process whereby the drug formulations are dispensed from the drug delivery device under force provided by the plugs within each reservoir. Accordingly, the term does not refer to the passive, chemical diffusion of the drug formulations out of the reservoir, although passive diffusion may contribute to release of the drug formulations from the porous membrane. As shown in FIGS. 7A-7B, the actuation system 738 may include a power source 740, a microcontroller 744, and an actuation mechanism 746. In certain embodiments, as shown in FIG. 9, first and second actuation systems 928, 929 are located at the actuation ends of the first and second reservoirs 914, 916. Embodiments having more than one actuation system may include multiple actuation mechanisms and a shared power source and microcontroller. Alternatively, embodiments having more than one actuation system may include multiple individual actuations systems, each having a power source, microcontroller, and actuation mechanism.

The power source may be any source of mechanical, electrical power or electromechanical power. The power source may include one or more batteries or fuel cells.

The microcontroller may be configured to control the actuation system of the device, and thereby control the timing of release of the drug formulations. For example, the microcontroller may selectively transmit electrical and/or mechanical power to the actuation mechanism, advancing the plugs through the reservoirs and dispensing the drug formulations. The microcontroller may be configured to control the timing of delivery of the drug formulations by applying the necessary electrical potentials to the actuation mechanism. The controller may be programmable or it may be pre-programmed to deliver the drug formulations in accordance with a prescribed (predetermined) release schedule.

The actuation mechanism may include fluid-volume displacement, mechanical displacement, osmotic swelling displacement, electrostatically-induced compression, piezoelectric actuation, thermally/magnetically induced phase transformation, or combinations thereof, to drive the plug via positive displacement.

In certain embodiments, the one or more actuation systems are each configured to generate a displacement fluid in operable communication with the first and/or second plugs to drive the first and/or second plugs. As shown in FIGS. 4B-4E, the actuation system 438 may be configured to generate a displacement fluid 448 in operable communication with first plug 422 and second plug 424 to drive the first and second plugs. For example, the plugs may drive the drug formulations toward the release end by a positive displacement process. The actuation system 438 may include an electrolytic cell 452 having a cathode and an anode which contact water or an aqueous solution to generate displacement a gas 448, such as oxygen, to drive the first and second drug formulations out of the first and second reservoirs, respectively.

Figure 8A:
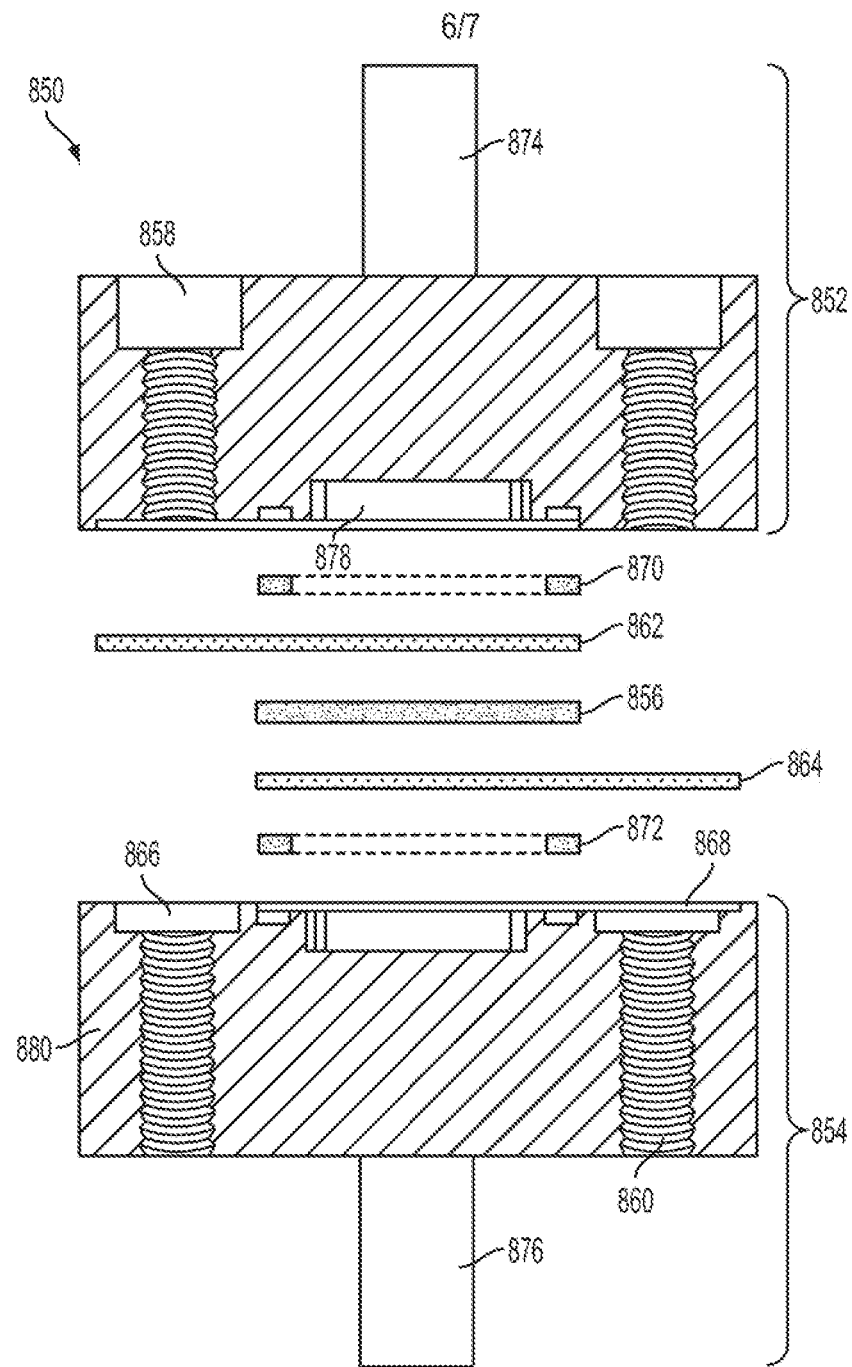
FIG. 8A is a partially exploded cross-sectional view, illustrating one embodiment of an electrolytic cell for us in an actuation system of one embodiment of a drug delivery device.
Figure 8B:
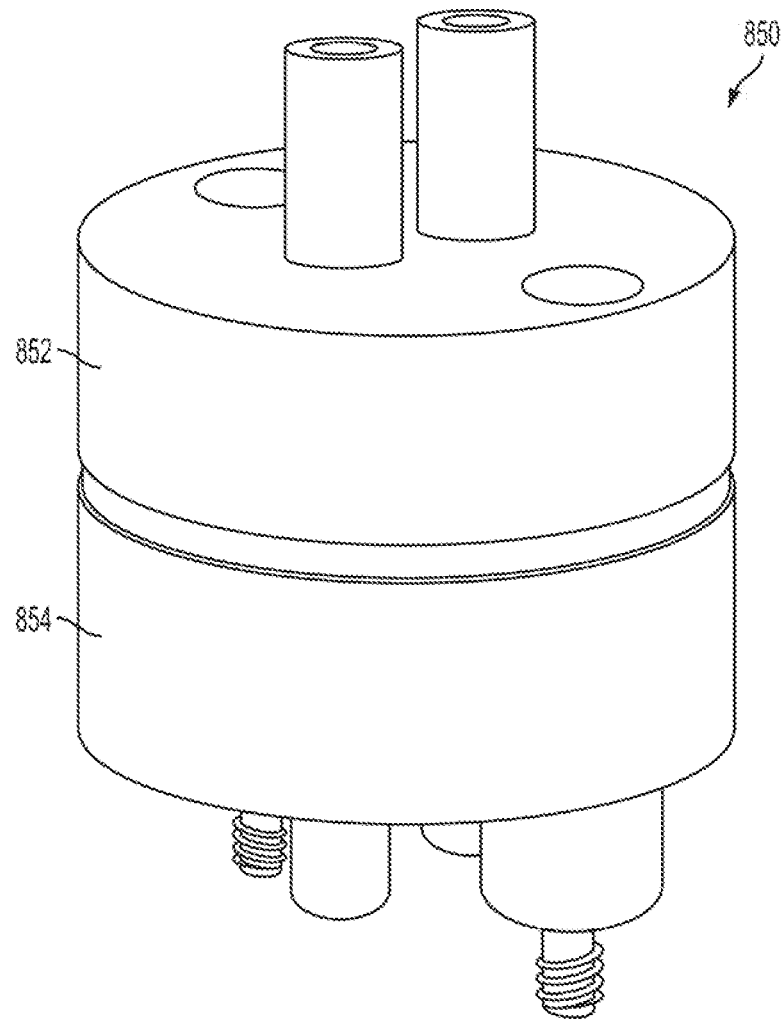
FIG. 8B is a perspective view, illustrating the electrolytic cell of FIG. 8A.

In certain embodiments, the one or more actuation systems each comprise an electrolytic cell. FIGS. 8A-8B show one embodiment of an electrolytic cell 850. The cell 850 includes cathode assembly 852 and anode assembly 854, which are assembled to be in intimate contact. The intimate contact may be achieved by chemical or thermal surface modification (including but not limited to epoxies and adhesives), mechanical compression (including but not limited to screw-based torque application), welding, soldering. In one embodiment, the units are assembled to be in intimate contact by means of chemical surface modification including but not limited to an epoxy-based seal. The electrode assembly units can be made of a variety of materials including but not limited to metals and polymers. In one embodiment, the units are made of a high volume manufacturing-compliant polymer, such as polypropylene. The electrodes may be made of a variety of materials including metallized substrates, conductive and/or metallized polymers. In one embodiment, the electrodes are made of porous planar metallized polymer substrates such as metallized polyester or metallized PEN.

Cathode assembly 852 and anode assembly 854 are arranged to be in contact with active component 856 on either side. The electrodes may be permeable to provide access to the active component, for example electrodes may include fabricated and/or naturally occurring macroscopic or microscopic pores. Gaseous products, such as $H_2$ and $O_2$, may be generated when energy is applied to the active component, including but not limited to electrical energy and thermal energy. For example, active component 856 may be a sulfonated tetrafluoroethylene based fluoropolymer-copolymer which is highly selective and permeable to water, such as Nafion. When electrical energy is applied to a hydrated Nafion layer $H_2$ and $O_2$ gases are generated by methods including but not limited to electrolysis of water. Other active components such as ionic solutions, hydrogels, $H_2O_2$, and other fluids that can be electrolyzed to generate gaseous products may also be used.

Electrical contact to the cathode and anode assemblies 852, 854 is achieved via screws 858, 860, perforated electrodes 862, 864 and nuts 866, 868. The components are arranged such that the screws 858, 860 are used for both fastening and providing isolated electrode contacts to the anode and cathode assembles 852, 854. A low-resistance and uniform electrical contact along the surface of the active component 856 may be achieved by using planar perforated electrodes 862, 864 having holes therein to allow the screws to pass through. The nuts 866, 868 serve as the electrical contact between the perforated electrodes and the screws. Other forms of electrical contact to the electrodes may also be used, such as flex-cables, for example metal on a flexible polymer substrate, printed circuit boards, screw-based contact, and soldering wires.

Gaseous isolation between the anode and cathode assemblies 852, 854 is achieved using compression-based gasket sealing with O-rings 870, 872, which are compressed by fastening the two assemblies 852, 854 together using screws 858, 860. Other methods of sealing such as epoxy and metallic weld/solder may also be used. Gas collection is achieved by directing the gas generated at the active component through conduits in the electrode assembly units into structures such as a nozzle or chamber. For example, at least one outlet port 874, 876 is provided at each of the anode and cathode assemblies 852, 854 for gas collection of $H_2$ and $O_2$, respectively, and to provide access to the active component between the electrodes. The outlet ports 874, 876 also provide water perfusion to hydrate the Nafion layer 856.

In order to ensure uniform hydration and gas collection from the active layer 856, the anode and cathode assemblies 852, 854 include flow-fields 878, 880 which help maximize the amount of gas generated and collected from the active layer. The flow-field pattern can be any shape or pattern configured to maximize the accessible area of the active layer 856, and thereby maximize the amount of gas produced and collected. For example, the flow-fields may include a meandering conduit. Gas-permeable substrates may also be used to maximize gas generation and collection.

FIG. 8B shows an assembled electrolytic cell 850. The cell may have a diameter of about 25.5 mm and a height of about 19 mm. Other dimensions are envisioned. The electrical connections to the anode and cathode are made on one side, namely the anode assembly 854 to ensure complete gaseous isolation at the cathode assembly 852.

In certain embodiments, a multi-actuator assembly can be made using multiple electrolytic cells spatially arranged within a single structure to allow for localized and isolated generation of gases at specified locations. The cells can be pre-assembled or assembled together in order to have intimate contact by methods such as chemical or thermal surface modification (including but not limited to epoxy and adhesives), mechanical compression (including but not limited to screw-based torque application), welding, and soldering. In one embodiment, the individual cells share the same active component. Activation may be achieved using separate electrode pairs for each cell or by using a shared electrode or electrodes. The gases generated may be collected and mixed between cells to produce a higher volume of gas at a particular location in the structure.

In one embodiment, a channel is provided in the housing to allow aqueous secretions from the mucosal tissue of the lumen to contact the cathode and anode. In one embodiment, water or an aqueous solution is contained on-board the device. For example, the actuation system may include a reservoir containing an electrolytic solution, for example an ionic solution such as sodium nitrite. In one embodiment, the actuation system includes a reservoir containing deionized water and a solid electrolyte contacting the surfaces of the cathode and anode.

An electrical potential of about 1.0 V or greater may be applied to the electrodes of the electrolytic cell to generate oxygen at the anode. The reaction at the anode is described by EQ. 1. In the water, at the negatively charged cathode, a reduction reaction takes place, with electrons from the cathode being given to the hydrogen cations to form hydrogen gas as shown in EQ. 2. The pressure exerted by the generated oxygen and hydrogen causes the plugs to advance through the reservoir, thereby causing the drug formulations to be released at the release ends of the reservoirs and into the lumen. While the pressure exerted on each plug is substantially equal, the plugs may be driven through the reservoirs at different rates based on reservoir and release end characteristics. For example, the reservoirs may each include distinct end caps or threshold barriers that provide differential back pressure within the reservoirs such that the same pressure exerted on the plugs results in the drug formulations being released from the reservoirs at different times or rates.

The production of oxygen and hydrogen may be controlled by the power source and a microcontroller that is programmed to supply an electrical potential to the cathode and anode at a selected time.

$$2H_2O(l) \rightarrow O_2(g) + 4H^+(aq) + 4e^- \qquad \text{EQ. 1}$$

$$2H^+(aq) + 2e^- \rightarrow H_2(g) \qquad \text{EQ. 2}$$

In other embodiments, the actuation system is configured to drive the plugs via positive displacement effectuated by the enlargement of a component within the actuation system, for example, a swellable material (such as a swellable gel) or an enlargeable repository. For example, the actuation system may include one or more of the actuation mechanisms as described in U.S. patent application Ser. No. 13/629,184, entitled "Drug Reconstitution and Delivery Device and Methods," which is filed concurrently herewith and the disclosure of which is incorporated herein by reference in its entirety. In some embodiments, the drug formulations are dispensed by osmotic swelling displacement. Optionally, one or more valves may be provided to selectively control the ingress of water into the repository or swellable material. Water from the lumen may be drawn into a repository or swellable material, causing the repository or swellable material to expand in volume. The expansion of the repository or swellable material may displace the drug formulations contained within the reservoir, causing the drug formulations to be dispensed from the device into the lumen. The actuation of the valve may be controlled by the microcontroller.

In other embodiments, the drug formulations are dispensed by an expansive force supplied by an induced phase transformation. For example, the actuation system may include an expandable repository containing a phase-transformable material. The phase-transformable material may be any liquid or solid that will undergo a phase transition from solid or liquid to gas when heated or subjected to an electro-magnetic field. For example, metals such as Ag—Cd 44/49 at. % Cd; Au—Cd 46.5/50 at. % Cd; Cu—Al—Ni 14/14.5 wt. % Al and 3/4.5 wt. % Ni; Cu—Sn approx. 15 at. % Sn; Cu—Zn 38.5/41.5 wt. % Zn; Cu—Zn—X (X=Si, Al, Sn); Fe—Pt approx. 25 at. % Pt; Mn—Cu 5/35 at. % Cu; Fe—Mn—Si; Pt alloys; Co—Ni—Al; Co—Ni—Ga; Ni—Fe—Ga; Ti—Pd in various concentrations; Ni—Ti (~55% Ni); Ni—Ti—Nb; and Ni—Mn—Ga will undergo a transform in response to thermal stress. For example, ferromagnetic materials and magnetic shape-memory alloys, for example $Ni_2MnGa$, transform in response to magnetic stress. For example, polymers such as polyurethanes, block copolymers such as those of polyethylene terephthalate (PET) and polyethyleneoxide (PEO), those containing polystyrene and poly(1,4-butadiene), ABA triblock copolymer made from poly(2-methyl-2-oxazoline), and polytetrahydrofuran, transform under external stress.

When the material transforms to a gas, the material expands and advances through the reservoir to dispense the drug formulations from the device. The actuation of the phase-transformation may be controlled by the microcontroller.

In other embodiments, the drug formulations are positively displaced and dispensed from the housing by electrostatically-induced compression or using a piezoelectric actuator. For example, a dielectric elastomeric actuator or piezoelectric actuator may be arranged such that a change in voltage or current to the actuator causes the actuator to exert a compressive force on the drug formulations in the reservoir. This compressive force may cause the drug formulations to be dispensed from the device. The actuation of the actuator may be controlled by the microcontroller.

In other embodiments, positive displacement of the drug formulations is achieved using a static pressure head and an actuatable valve. The valve may be operated, for example, in an analog mode for amplitude-modulated dosing or it may be operated in a digital mode for frequency/duty-cycle modulated dosing. The static head pressure may be provided by loading the drug formulations into the device under pressure or the device may be pressurized after the drug formulations are loaded in the device.

In other embodiments, positive displacement of the drug formulations is achieved by mechanical displacement. For example, the mechanical displacement may involve a piston, a spring, or a combination thereof.

In certain embodiments, the actuation system further includes a wireless receiver for receiving wireless control signals from a separate, detached transmitting device. The device may be deployed into the lumen by the patient, physician, veterinarian, or the like, and thereafter, the patient, physician, veterinarian, or the like, may actuate the release of the drug formulations using the transmitting device to transmit control signals to the deployed device. Furthermore, in some embodiments, the receiver and transmitting device may both be transceivers capable of transmitting and receiving control signals and other communications from each other. Accordingly, in certain embodiments, the transceiver may transmit data relevant to the operation of the device, such as data regarding the drug formulations already administered, the release schedule, the amount of drug formulations remaining in the reservoir, and the remaining battery charge, as well as data relevant to the environment of the lumen, such as data detected or measured by an integral sensor. In some embodiments, the actuation system may also be wirelessly powered.

In certain embodiment, the device may is configured for wireless operation, e.g., following deployment in the human or animal subject. In such cases, the device includes appropriate telemetry components as known in the art. For example, actuation of the drug formulation dispensing may be done from a remote controller, e.g., external to the human or animal subject. Generally, the telemetry (i.e. the transmitting and receiving) is accomplished using a first coil to inductively couple electromagnetic energy to a matching/corresponding second coil. The means of doing this are well established, with various modulation schemes such as amplitude or frequency modulation used to transmit the data on a carrier frequency. The choice of the carrier frequency and modulation scheme will depend on the location of the device and the bandwidth required, among other factors. Other data telemetry systems known in the art also may be used. In another case, the device is configured to be remotely powered, or charged. For example, the device may include a transducer for receiving energy wirelessly transmitted to the device, circuitry for directing or converting the received power into a form that can be used or stored, and if stored, a storage device, such as a rechargeable battery or capacitor. In still another case, the device is both wirelessly powered and wirelessly controlled.

In some embodiments, the actuation system may further include one or more sensors for analyzing the environment around the device or within the lumen. For example, a sensor may be employed to detect the temperature or the presence of a drug-degrading enzyme in the lumen. In such embodiments, the microcontroller may be further configured to dispense the drug formulations after the abatement of the drug-degrading enzyme is detected or other suitable environmental conditions are detected for drug delivery.

Drug Formulations

One or more drug formulations are contained within the device reservoirs for delivery to the mucosal tissue. In one embodiment, two drug formulations are disposed within two reservoirs for release to a subject. In another embodiment, as shown in FIG. 6, three drug formulations 618, 620, 636 are disposed within reservoirs 614, 616, 634 for release to a subject.

Various drug formulations may be administered from the drug delivery device. The drug formulations within each reservoir may each include the same drug, may each include different drugs, or may be some combination of more than one similar drug and more than one different drug. For example, the first drug formulation may include a different drug than the second drug formulation. For example, the first and third drug formulations may both include the same drug, and second drug formulations may include a different drug than the first and third drug formulations.

In certain embodiments, the device may be used to deliver a battery of drug formulations for a combination therapy, prophylaxis, or for another specific treatment, such as may be useful in animal husbandry.

In one embodiment, the device is used to deliver a fixed time artificial insemination treatment to a human or animal subject. In certain embodiments, the first drug formulation includes a gonadotropin-releasing hormone, the second drug formulation includes a prostaglandin, and the third drug formulation includes a gonadotropin-releasing hormone. In one embodiment, the device also includes a fourth drug formulation which includes a progestin. Variations of the drugs and sequences are envisioned.

In embodiments, the drug formulations include one or more proteins or peptides. For example, in some embodiments, the drug delivery device may be used to administer hormones or steroids. including, but not limited to, follicle stimulating hormone, parathyroid hormone, luteinizing hormone, gonadotropin-releasing hormone (GnRH), estradiol, progesterone, melatonin, serotonin, thyroxine, triiodothyronine, epinephrine, norepinephrine, dopamine, antimullerian hormone, adiponectin, adrenocorticotropic hormone, angiotensinogen, angiotensin, antidiuretic hormone, atrial-natriuretic peptide, calcitonin, cholecystokinin, corticotropin-releasing hormone, erythropoietin, gastrin, ghrelin, glucagon, growth hormone-releasing hormone, human chorionic gonadotropin, human placental lactogen, growth hormone, inhibin, insulin, insulin-like growth factor, leptin, melanocyte stimulating hormone, orexin, oxytocin, prolactin, relaxin, secretin, somatostatin, thrombopoietin, thyroid-stimulating hormone, thyrotropin-releasing hormone, cortisol, aldosterone, testosterone, dehydroepiandrosterone, androstenedione, dihydrotestosterone, estrone, estriol, calcitriol, calcidiol, prostaglandins, leukotrienes, prostacyclin, thromboxane, prolactin releasing hormone, lipotropin, brain natriuretic peptide, neuropeptide Y, histamine, endothelin, enkephalin, renin, and pancreatic polypeptide.

In some embodiments, the drug delivery device may be used to administer cytokine signaling molecules or immunomodulating agents that are used in cellular communication. These molecules commonly comprise proteins, peptides, or glycoproteins. Cytokine signaling molecules include, for example, the four α-helix bundle family which include the IL-2 subfamily (e.g., erythropoietin (EPO) and thrombopoietin (THPO)), the interferon (IFN) subfamily and the IL-10 subfamily. Cytokine signaling molecules also include the IL-1, IL-18, and IL-17 families.

In some embodiments, the drug delivery device may be used to administer drug formulations for pain management, including, but not limited to, corticosteroids, opioids, antidepressants, anticonvulsants (antiseizure medications), nonsteroidal anti-inflammatory drugs, COX2 inhibitors (e.g., rofecoxib and celecoxib), ticyclic antidepressants (e.g., amitriptyline), carbamazepine, gabapentin and pregabalin, codeine, oxycodone, hydrocodone, diamorphine, and pethidine.

In some embodiments, the drug delivery device may be used to administer cardiovascular drug formulations. Examples include B-type natriuretic peptide (BNP), atrial natriuretic peptide (ANP), atrial natriuretic factor (ANF), atrial natriuretic hormone (ANH), and atriopeptin. Cardiovascular drug formulations that may be administered by the device also include, for example, antiarrhythmic agents, such as Type I (sodium channel blockers), including quinidine, lidocaine, phenytoin, propafenone; Type II (beta blockers), including metoprolol; Type III (potassium channel blockers), including amiodarone, dofetilide, sotalol; Type IV (slow calcium channel blockers), including diltiazem, verapamil; Type V (cardiac glycosides), including adenosine and digoxin. Other cardiacvascular drug formulations that may be administered by the device include ACE inhibitors, such as, for example, captopril, enalapril, perindopril, ramipril; angiotensin II receptor antagonists, such as, for example, candesartan, eprosartan, irbesartan, losartan, telmisartan, valsartan; beta blocker; and calcium channel blocker.

The drug formulations may be formulated with one or more pharmaceutically acceptable excipients as needed to facilitate the drug's storage in and release from the device. In one embodiment, the drug may be in a liquid solution or suspension. The drug may be in the form of microparticles or nanoparticles. The solvent or carrier may be aqueous or organic. For example, the devices and methods described herein may further include a reconstitution mechanism as described in U.S. patent application Ser. No. 13/629,184, entitled "Drug Reconstitution and Delivery Device and Methods," which is filed concurrently herewith and the disclosure of which is incorporated herein by reference in its entirety.

In some embodiments, the drug formulations may include components that are degradable by the enzymes present in the fluid secreted by the mucosal tissue. For example, certain amino acids present in drug formulations may be degraded by the enzymes present in fluid secreted by the mucosal tissue. Accordingly, the devices and methods described herein may further include one or more of the permeation enhancement mechanisms described in U.S. Patent Application Publications No. 2011/0087195, No. 2011/0087192, and No. 2011/0087155, the disclosures of which are incorporated herein by reference in pertinent part.

Methods

Methods are provided for transmucosal drug delivery using intraluminal devices. The intraluminal devices may include any of the device features described herein. The methods include deploying a drug delivery device into the mucosal lumen of a human or animal subject. For example, the subject may be a mammalian animal (e.g., cow, sheep, horse, pig, or dog). The methods include various medical and veterinary therapies, as well as animal husbandry applications. The lumen may be, for example, a vagina, cervix, uterus, bladder, or rectum. The device may be adapted to contact essentially any mucosal tissue surface. The device may be placed in the lumen by inserting the device through an exterior orifice of the patient into the lumen. In some embodiments, the device may be in a form that may be orally administered for delivery of a drug via the mucosal tissue of the gastrointestinal tract.

The drug delivery device includes a first and second reservoirs containing first and second drug formulations, respectively. The drug delivery device also includes a porous membrane sidewall. After the drug delivery device is placed in the mucosal lumen, one or more actuation systems are actuated to drive the first and second drug formulations out of the first and second reservoirs and into the porous membrane sidewall. The first and second drug formulations are released from the porous membrane sidewall to the mucosal lumen adjacent thereto.

In certain embodiments, a single actuation system is actuated to drive the first drug formulation out of the first reservoir and thereafter, the single actuation system is actuated to drive the second drug formulation out of the second reservoir.

The first drug formulation may be completely or partially released from the first reservoir before the release of the second drug formulation from the second reservoir.

As illustrated in FIG. 1, the drug delivery device 100 may be placed in a lumen 126. The drug delivery device may be held in place by frictional engagement between the mucosal tissue and the housing. As shown in FIGS. 7A-7B, arms 750 may be provided to facilitate retention of the device within the mucosal lumen. As shown in FIG. 7C, the drug formulations may then be driven out of the reservoirs and into the porous membrane sidewall 742 from which the drug formulations are then released to the mucosal lumen. The actuation of the actuation system may be controlled by the microcontroller 744. The device may thereafter be removed from the lumen.

A microcontroller may actuate the delivery of the drug formulations by applying an electrical potential to the cathode and the anode of at least one electrolytic cell to generate a gas to drive the drug formulations out of the reservoirs. As illustrated in FIGS. 4B-4E, as gas 448 is generated by the electrolytic cell 452 of actuation system 438, the first and second plugs 422, 424 advance through the first and second reservoirs 414, 416 causing the first and second drug formulations 418, 420 to be driven out of the reservoirs. The device may thereafter be removed from the lumen.

In another aspect, a method of fixed time artificial insemination is provided. The method may include (a) deploying a drug delivery device into a vaginal lumen of an animal subject, wherein the device has a housing containing (i) a first reservoir containing a first drug formulation, (ii) a second reservoir containing a second drug formulation, (iii) a third reservoir containing a third drug formulation, (iv) a porous membrane sidewall adjacent the vaginal lumen, and (v) one or more actuation systems configured to drive the first, second, and third drug formulations from the first, second, and third reservoirs; (b) driving the first drug formulation out of the first reservoir at a first time; (c) driving the second drug formulation out of the second reservoir at a second time, which is after the first time; (d) driving the third drug formulation out of the third reservoir at a third time, which is after the second time; and (e) artificially inseminating the animal subject at a fourth time, which is after the third time. In one embodiment, the first drug formulation includes a gonadotropin-releasing hormone, the second drug formulation includes a prostaglandin, and the third drug formulation includes a gonadotropin-releasing hormone.

The drug delivery devices may include any of the device features described herein. For example, the device may include a microcontroller configured to control the actuation system, and thereby control the timing of the release of the drug formulations.

In certain embodiments, the method of fixed time artificial insemination further includes releasing from a fourth reservoir a fourth drug formulation including a progestin at a fifth time either before the first time or between the first and second times. In one embodiment, the first time is a time after deployment of the drug delivery device, the second time is from about 5 days to about 7 days after the first time, the third time is from about 2 days to about 3 days after the second time, and the fourth time is either coincident with the third time or from about 8 hours to about 16 hours after the third time.

Applications/Uses

The drug delivery devices and methods may be used for various medical and therapeutic applications in human and animal subjects, as well as in animal husbandry.

In some embodiments, the drug delivery device may be used to treat infertility or provide a fixed time artificial insemination (FTAI) treatment in a female subject. For example, the drug delivery device may be placed in the vagina (or uterus, or other part of the birth canal) of a female subject. The drug delivery device may then deliver follicle stimulating hormone to induce ovulation in the female subject. In some embodiments, the drug delivery device may be configured to deliver a plurality of hormones, including follicle stimulating hormone, luteinizing hormone, gonadotropin-releasing hormone separately, or in combination, in appropriate sequences, at appropriate times, and in pharmacologically appropriate amounts. The device may also dispense estradiol to regulate natural hormone production in the female subject. The appropriate dosing schedule and amounts may be determined by one in the field of reproductive pharmacology.

Compared to traditional FTAI treatments, the methods described herein require only device implantation and removal at the time of artificial insemination, and result in a 50% reduction in time spent driving, herding and chuting cattle. The methods also result in improved ovulation quality and quantity due to the reduction in handling, stress, and systemic cortisol levels of the subjects. The methods also reduce the number of medical supplies needed, as a single device delivery the series of FTAI drugs.

In another embodiment, the drug delivery device may be used to treat insulin dependent diabetes (Type I diabetes) in a subject. The drug delivery device may be placed within a lumen of the subject. The drug delivery device may then deliver insulin (Humulin R, Novolin R), insulin isophane (Humulin N, Novolin N), insulin lispro (Humalog), insulin aspart (NovoLog), insulin glargine (Lantus) or insulin detemir (Levemir) to the patient at a selected time or times.

In another embodiment, the drug delivery device may be used to treat diabetes mellitus (Type II diabetes) in a subject. The drug delivery device may be placed within a lumen of the subject. The drug delivery device may then deliver exenatide to the patient at a selected time or times.

In another embodiment, the drug delivery device may be used to treat breast or ovarian cancer in a subject. The drug delivery device may be placed within a lumen of the subject, such as the vagina for a female subject. The drug delivery device may then deliver abraxane (or other drug effective in the treatment or management of cancer) to the patient at a selected time or times.

In another embodiment, the drug delivery device may be used to treat HIV/AIDS in a subject. The drug delivery device may be placed within a lumen of the subject. The drug delivery device may then deliver Abacavir (ABC) or Cidofovir (or other drug effective in the treatment or management of HIV/AIDS) to the patient at a selected time or times. The device also may be used to treat other sexually transmitted diseases.

In another embodiment, the drug delivery device may be used to treat genital herpes in a subject. The drug delivery device may be placed within a lumen of the subject, such as within the vagina of a female subject. The drug delivery device may then deliver acyclovir, famciclovir, or valacyclovir (or other drug effective in the treatment or management of genital herpes) to the patient at a selected time or times.

In another embodiment, the drug delivery device may be used to treat diabetes insipidus in a subject. The drug delivery device may be placed within a lumen of the subject. The drug delivery device may then deliver desmopressin (or other drug effective in the treatment or management of diabetes insipidus) to the patient at a selected time or times.

In another embodiment, the drug delivery device may be used to treat osteoporosis in a subject. The drug delivery device may be placed within a lumen of the subject, such as within the vagina of a female subject. The drug delivery device may then deliver ibandronate, calcitonin, or parathyroid hormone (or other drug effective in the treatment or management of osteoporosis) to the patient at a selected time or times.

It will be appreciated that various of the above-disclosed and other features and functions, or alternatives thereof, may be desirably combined into many other different devices, methods, or applications. Various presently unforeseen or unanticipated alternatives, modifications, variations, or improvements therein may be subsequently made by those skilled in the art which are also intended to be encompassed by the following claims.

We claim:

1. A method of fixed time artificial insemination comprising:
   deploying a drug delivery device into a vaginal lumen of an animal subject, wherein the device comprises a housing containing (i) a first reservoir containing a first drug formulation comprising a gonadotropin-releasing hormone, (ii) a second reservoir containing a second drug formulation comprising a prostaglandin, (iii) a third reservoir containing a third drug formulation comprising a gonadotropin-releasing hormone, (iv) a porous membrane sidewall adjacent the vaginal lumen, and (v) one or more actuation systems configured to drive the first, second, and third drug formulations from the first, second, and third reservoirs;
   thereafter driving the first drug formulation out of the first reservoir at a first time;
   driving the second drug formulation out of the second reservoir at a second time, which is after the first time;
   driving the third drug formulation out of the third reservoir at a third time, which is after the second time; and
   artificially inseminating the animal subject at a fourth time, which is after the third time, wherein the porous membrane sidewall comprises a fluidic valve configured such that a critical threshold pressure from about 0.1 psi to about 100 psi is required to drive the first, second, and third drug formulations from the first, second, and third reservoirs to the vaginal lumen.

2. The method of claim 1, wherein the first time is a time after the deployment of the drug delivery device, the second time is from about 5 days to about 7 days after the first time, the third time is from about 2 days to about 3 days after the second time, and the fourth time is either coincident with the third time or from about 8 hours to about 16 hours after the third time.

3. The method of claim 1, wherein the device further comprises a fourth reservoir containing a fourth drug formulation comprising a progestin, and the method further comprises driving the fourth drug formulation out of the fourth reservoir at a fifth time either before the first time or between the first and second times.

4. The method of claim 1, wherein
   the first reservoir contains a first plug, the second reservoir contains a second plug, and the third reservoir contains a third plug, and
   driving the drug formulations out of the reservoirs comprises driving the plugs so as to drive the drug formulations out of the reservoirs.

5. A method of fixed time artificial insemination comprising:
   deploying a drug delivery device into a vaginal lumen of an animal subject, wherein the device comprises a housing containing (i) a first reservoir containing a first drug formulation comprising a gonadotropin-releasing hormone, (ii) a second reservoir containing a second drug formulation comprising a prostaglandin, (iii) a third reservoir containing a third drug formulation comprising a gonadotropin-releasing hormone, (iv) a porous membrane sidewall adjacent the vaginal lumen, and (v) one or more actuation systems configured to drive the first, second, and third drug formulations from the first, second, and third reservoirs;

thereafter driving the first drug formulation out of the first reservoir at a first time;

driving the second drug formulation out of the second reservoir at a second time, which is after the first time;

driving the third drug formulation out of the third reservoir at a third time, which is after the second time; and artificially inseminating the animal subject at a fourth time, which is after the third time, wherein the porous membrane sidewall substantially surrounds the housing about the first, second, and third reservoirs.

6. The method of claim 5, wherein the porous membrane sidewall is cylindrical.

7. The method of claim 5, wherein:

the first, second, and third reservoirs each comprise a release end and an opposed actuation end in communication with the one or more actuation systems, and the porous membrane sidewall comprises a first portion adjacent the release ends of the reservoirs and a second portion adjacent the actuation ends of the reservoirs such that the drug formulations are distributed from both the first and second portions of the porous membrane sidewall.

8. The method of claim 5, wherein the first time is a time after the deployment of the drug delivery device, the second time is from about 5 days to about 7 days after the first time, the third time is from about 2 days to about 3 days after the second time, and the fourth time is either coincident with the third time or from about 8 hours to about 16 hours after the third time.

9. The method of claim 5, wherein the device further comprises a fourth reservoir containing a fourth drug formulation comprising a progestin, and the method further comprises driving the fourth drug formulation out of the fourth reservoir at a fifth time either before the first time or between the first and second times.

10. The method of claim 5, wherein the first reservoir contains a first plug, the second reservoir contains a second plug, and the third reservoir contains a third plug, and driving the drug formulations out of the reservoirs comprises driving the plugs so as to drive the drug formulations out of the reservoirs.

\* \* \* \* \*